United States Patent
Dong et al.

(10) Patent No.: US 10,294,191 B2
(45) Date of Patent: May 21, 2019

(54) MONOPHOSPHINE COMPOUNDS AND PALLADIUM CATALYSTS BASED THEREON FOR THE ALKOXYCARBONYLATION OF ETHYLENICALLY UNSATURATED COMPOUNDS

(71) Applicant: EVONIK DEGUSSA GMBH, Essen (DE)

(72) Inventors: Kaiwu Dong, Bo Zhou (CN); Ralf Jackstell, Cuxhaven Altenwalde (DE); Matthias Beller, Ostseebad Nienhagen (DE); Robert Franke, Marl (DE); Dieter Hess, Marl (DE); Katrin Marie Dyballa, Recklinghausen (DE); Dirk Fridag, Haltern am See (DE); Frank Geilen, Haltern am See (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/213,449

(22) Filed: Jul. 19, 2016

(65) Prior Publication Data
US 2017/0022139 A1   Jan. 26, 2017

(30) Foreign Application Priority Data

Jul. 23, 2015   (DE) .................... 10 2015 213 918

(51) Int. Cl.
| | | |
|---|---|---|
| C07F 15/00 | (2006.01) |
| C07F 9/28 | (2006.01) |
| B01J 27/185 | (2006.01) |
| C07C 67/38 | (2006.01) |
| C07F 9/58 | (2006.01) |
| C07F 9/572 | (2006.01) |
| C07F 9/6506 | (2006.01) |
| B01J 31/24 | (2006.01) |
| B01J 31/22 | (2006.01) |
| C07F 9/655 | (2006.01) |

(Continued)

(52) U.S. Cl.
CPC .......... *C07C 67/38* (2013.01); *B01J 31/2295* (2013.01); *B01J 31/24* (2013.01); *B01J 31/2404* (2013.01);
(Continued)

(58) Field of Classification Search
CPC .......... C07F 15/00; C07F 9/28; B01J 27/185
(Continued)

(56) References Cited

U.S. PATENT DOCUMENTS 5,028,576 A * 7/1991 Drent ................... B01J 31/0208
502/162
5,166,330 A * 11/1992 Engels .................. C07F 9/4883
536/26.3
5,268,479 A    12/1993 Stelzer et al.

FOREIGN PATENT DOCUMENTS

DE    4141229 A1    6/1993
EP    0386834 A1    9/1990
(Continued)

OTHER PUBLICATIONS

Schwedtmann, K. et al.: Synthesis and EPR/UV/Vis-NIR spectroelectrochemical investigation of a persiistent phosphanyl radical dication. Angew. Chem. Int. Ed., vol. 54, pp. 11054-11058, 2015.*
Brodie, N. et al.: Synthesis and X-ray crystal structure of Dipalladiumtetrachlorobis(ethyldipyrrolylphosphine). vol. 33, pp. 1739-1745, 1998.*
(Continued)

*Primary Examiner* — Charanjit Aulakh
(74) *Attorney, Agent, or Firm* — Smith, Gambrell & Russell, LLP

(57) ABSTRACT

The invention relates to compounds of formula (I)

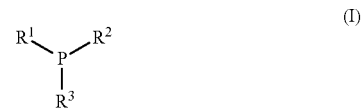

where
$R^1$ is selected from —$(C_1$-$C_{12})$-alkyl, —$(C_3$-$C_{12})$-cycloalkyl, —$(C_3$-$C_{12})$-heterocycloalkyl;
$R^2$ is selected from —$(C_3$-$C_{12})$-heterocycloalkyl, —$(C_6$-$C_{20})$-aryl, —$(C_3$-$C_{20})$-heteroaryl;
$R^3$ is —$(C_3$-$C_{20})$-heteroaryl;
and $R^1$, $R^2$ and $R^3$ may each independently be substituted by one or more substituents selected from
—$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —COO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, halogen.
The invention further relates to Pd complexes comprising the compound according to the invention and to the use thereof in alkoxycarbonylation.

10 Claims, No Drawings

(51) Int. Cl.
   *C07F 9/6553* (2006.01)
   *C07F 17/02* (2006.01)

(52) U.S. Cl.
   CPC ........... *B01J 31/2409* (2013.01); *C07F 9/572* (2013.01); *C07F 9/58* (2013.01); *C07F 9/6506* (2013.01); *C07F 9/65515* (2013.01); *C07F 9/655345* (2013.01); *C07F 15/006* (2013.01); *C07F 17/02* (2013.01); *B01J 2231/321* (2013.01); *B01J 2231/49* (2013.01); *B01J 2531/0208* (2013.01); *B01J 2531/824* (2013.01); *B01J 2531/842* (2013.01)

(58) Field of Classification Search
   USPC ............. 548/101, 111; 502/213, 171; 546/21
   See application file for complete search history.

(56) References Cited

FOREIGN PATENT DOCUMENTS

| | | |
|---|---|---|
| EP | 0441446 A1 | 8/1991 |
| EP | 0441447 A1 | 8/1991 |

OTHER PUBLICATIONS

Dabokowski, W. et al.: A convenient synthesis of phosphorus and sulfonyl-substituted N-imidazoles (triazoles) using the corresponding acid chlorides and N-trimethylsilyl imidazoles (tiazoles).vol. 26, pp. 321-326, 1986.*

Search Report dated Jan. 2, 2017 for EP 16180043 (11 pages).

Goudriaan et al. Synthesis of building blocks for the development of the SUPRAPhos ligand library and examples of their application in catalysis. European Journal of Organic Chemistry, 2008, 6079-6092.

Goryunov et al. Compounds $R^1R^2EMMe_3$ (E=P, As; M=Si, Sn)—Convenient and Versatile Reagents for the Syntheses of Tertiary (Fluoroaryl)phosphanes and -arsanes. Collection of Czechoslovak Chemical Communications, 2008, vol. 73, No. 12,1612-1622.

Blank et al. Palladium-Catalyzed Asymmetric Phosphination. Scope, Mechanism, and Origin of Enantioselectivity. Journal of the American Chemical Society, 2007,129, 6847-6858.

Green et al. Palladium(II) complexes of new OPN phosphine ligands and their application in homogeneously catalysed reactions of CO with alkenes or alkynes. Dalton Transactions: The International Journal for Inorganic, Organometallic and Bioinorganic Chemistry, 2004. 3251-3260.

Kuang et al: Formation of donor-acceptor Fe(0)—Hg(II) bond in separation and stabilization of optically active iron(0) phosphine complexes. Absolute configuration of (+)-(R)-(C0)$_4$Fe(μ-EtPhPpy)HgCl$_2$. Inorganica Chimica Acta, 293, 1999, 106-109.

Kuang et al. Coordination chemistry of organometallic polydentate ligands. Syntheses of Fe—M complexes using Fe(CO)$_4$(Ph$_2$Ppy-P)[Ph$_2$Ppy=2-(Diphenylphosphino)Pyridine] and Trans-Fe(PhPMepy)$_2$(CO)$_3$[PhPMepy=2-(Phenylrnethylphosphino)Pyridine] as a Neutral Bi- or Tridentate Ligand. Polyhedron, 1996, vol. 15, No. 19, 3417-3426.

Khokarale, S. G. et al. Zwitterion enhanced performance in palladium-phosphine catalyzed ethylene methoxycarbonylation. Catalysis Communications 44, 2014, pp. 73-75.

Fang, Xianjie et al., Palladium-Catalyzed Alkoxycarbonylation of Conjugated Dienes under Acid-Free Conditions: Atom-Economic Synthesis of β,γ-Unsaturated Esters. Angew. Chem. Int. Ed., 2014, 53, 9030-9034.

Armarego, Wilfred L.F., et al. Purification of Laboratory Chemicals, Butterworth Heinemann (Elsevier), 6th edition, Oxford 2009. (index provided).

Harris, Robin K. et al. NMR Nomenclature, Nuclear Spin Properties and Conventions for Chemical Shifts. Pure Appl. Chem., 2001, 73, pp. 1795-1818.

Harris, Robin K. et al. Further Conventions for NMR Shielding and Chemical Shifts. Pure Appl. Chem., 2008, 80, pp. 59-84.

Köppe, Ralf, et al. Quntenchemische und Experimentelle Untersuchungen zur Stabilität und Struktur von GaAs$_5$ und InAs$_5$. Angew. Chem. 2004, 43, 2222-2226.

Budzelaar, Peter H.M. et al. Synthesis and Coordination Chemistry of a New Class of Binucleating Ligands: Pyridyl-Substituted Diphosphines. Organometallics 1990, 9, 1222-1227.

U.S. Appl. No. 15/213,435, filed Jul. 19, 2016, Jennerjahn, et al.
U.S. Appl. No. 15/213,441, filed Jul. 19, 2016, Dong, et al.
U.S. Appl. No. 15/213,444, filed Jul. 19, 2016, Dong, et al.
U.S. Appl. No. 15/213,453, filed Jul. 19, 2016, Dong, et al.
U.S. Appl. No. 15/213,456, filed Jul. 19, 2016, Dong, et al.

* cited by examiner

MONOPHOSPHINE COMPOUNDS AND PALLADIUM CATALYSTS BASED THEREON FOR THE ALKOXYCARBONYLATION OF ETHYLENICALLY UNSATURATED COMPOUNDS

The present invention relates to novel monophosphine compounds and to the use thereof in alkoxycarbonylation.

The alkoxycarbonylation of ethylenically unsaturated compounds is a process of increasing significance. An alkoxycarbonylation is understood to mean the reaction of ethylenically unsaturated compounds, such as olefins, with carbon monoxide and alcohols in the presence of a metal or of a metal complex and a ligand to give the corresponding esters:

Scheme 1: General reaction equation of the alkoxycarbonylation of an ethylenically unsaturated compound

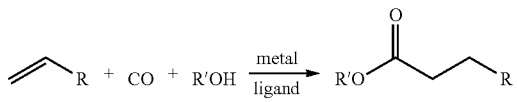

Among the alkoxycarbonylation reactions, the ethene methoxycarbonylation to give 3-methylpropionate is of significance as an intermediate stage for the preparation of methyl methacrylate (S. G. Khokarale, E. J. García-Suárez, J. Xiong, U. V. Mentzel, R. Fehrmann, A. Riisager, Catalysis Communications 2014, 44, 73-75). Ethene methoxycarbonylation is conducted in methanol as solvent under mild conditions with a palladium catalyst modified by phosphine ligands.

Alkoxycarbonylation can lead to branched (iso) or linear (n) products. Thus, not only the yield but also the n/iso selectivity is an important parameter in the development of novel catalytic systems for alkoxycarbonylation.

It is known that monophosphine compounds can be used as ligands for alkoxycarbonylation. One example of this is the alkoxycarbonylation of isoprene with benzyl alcohol in the presence of a Pd complex. In this reaction, for example, good yields have been achieved using the N-phenyl-2-(di-tert-butylphosphino)pyrrole ligand available under the cataCXium PtB trade name (Fang X. et al., Angew. Chem. Int. Ed., 2014, 53, 9030-9034). However, this ligand achieves only low selectivity. Similar heteroaryl-substituted monophosphine compounds, namely N-phenyl-2-(diphenylphosphino)pyrrole and N-phenyl-2-(dicyclohexylphosphino)pyrrole, have likewise been examined, but achieve only low yields in the alkoxycarbonylation of isoprene with benzyl alcohol (Fang X. et al., loc. cit.).

The problem addressed by the present invention is that of providing novel ligands for alkoxycarbonylation, with which a high yield and high n/iso selectivity can be achieved. More particularly, the ligands are to be suitable for the alkoxycarbonylation of long-chain ethylenically unsaturated compounds, for example $C_8$ olefins.

This problem is solved by monophosphine compounds of formula (I)

(I)

where $R^1$ is selected from $-(C_1-C_{12})$-alkyl, $-(C_3-C_{12})$-cycloalkyl, $-(C_3-C_{12})$-heterocycloalkyl;

$R^2$ is selected from $-(C_3-C_{12})$-heterocycloalkyl, $-(C_6-C_{20})$-aryl, $-(C_3-C_{20})$-heteroaryl;

$R^3$ is $-(C_3-C_{20})$-heteroaryl;

and $R^1$, $R^2$ and $R^3$ may each independently be substituted by one or more substituents selected from $-(C_1-C_{12})$-alkyl, $-(C_3-C_{12})$-cycloalkyl, $-(C_3-C_{12})$-heterocycloalkyl, $-O-(C_1-C_{12})$-alkyl, $-O-(C_1-C_{12})$-alkyl-$(C_6-C_{20})$-aryl, $-O-(C_3-C_{12})$-cycloalkyl, $-S-(C_1-C_{12})$-alkyl, $-S-(C_3-C_{12})$-cycloalkyl, $-COO-(C_1-C_{12})$-alkyl, $-COO-(C_3-C_{12})$-cycloalkyl, $-CONH-(C_1-C_{12})$-alkyl, $-CONH-(C_3-C_{12})$-cycloalkyl, $-CO-(C_1-C_{12})$-alkyl, $-CO-(C_3-C_{12})$-cycloalkyl, $-N-[(C_1-C_{12})$-alkyl]$_2$, $-(C_6-C_{20})$-aryl, $-(C_6-C_{20})$-aryl-$(C_1-C_{12})$-alkyl, $-(C_6-C_{20})$-aryl-$O-(C_1-C_{12})$-alkyl, $-(C_3-C_{20})$-heteroaryl, $-(C_3-C_{20})$-heteroaryl-$(C_1-C_{12})$-alkyl, $-(C_3-C_{20})$-heteroaryl-$O-(C_1-C_{12})$-alkyl, $-COOH$, $-OH$, $-SO_3H$, $-NH_2$, halogen.

The monophosphine compounds according to the invention are suitable as ligands for Pd complexes, with which high yields can be achieved in the alkoxycarbonylation of a multitude of ethylenically unsaturated compounds. More particularly, the compounds according to the invention are suitable for alkoxycarbonylation of ethene and long-chain olefins such as 1-octene.

The expression $(C_1-C_{12})$-alkyl encompasses straight-chain and branched alkyl groups having 1 to 12 carbon atoms. These are preferably $(C_1-C_8)$-alkyl groups, more preferably $(C_1-C_6)$-alkyl, most preferably $(C_1-C_4)$-alkyl.

Suitable $(C_1-C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethyl-pentyl, 1-propylbutyl, n-octyl, 2-ethylhexyl, 2-propylheptyl, nonyl, decyl.

The elucidations relating to the expression $(C_1-C_{12})$-alkyl also apply particularly to the alkyl groups in $-O-(C_1-C_{12})$-alkyl, $-S-(C_1-C_{12})$-alkyl, $-COO-(C_1-C_{12})$-alkyl, $-CONH-(C_1-C_{12})$-alkyl, $-CO-(C_1-C_{12})$-alkyl and $-N-[(C_1-C_{12})$-alkyl]$_2$.

The expression $(C_3-C_{12})$-cycloalkyl encompasses mono-, bi- or tricyclic hydrocarbyl groups having 3 to 12 carbon atoms. Preferably, these groups are $(C_5-C_{12})$-cycloalkyl.

The $(C_3-C_{12})$-cycloalkyl groups have preferably 3 to 8, more preferably 5 or 6, ring atoms.

Suitable $(C_3-C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3-C_{12})$-cycloalkyl also apply particularly to the cycloalkyl groups in $-O-(C_3-C_{12})$-cycloalkyl, $-S-(C_3-C_{12})$-cycloalkyl, $-COO-(C_3-C_{12})$-cycloalkyl, $-CONH-(C_3-C_{12})$-cycloalkyl, $-CO-(C_3-C_{12})$-cycloalkyl.

The expression $(C_3-C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3-C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A ($C_3$-$C_{12}$)-heterocycloalkyl group in the context of this invention is thus also ethylene oxide.

Suitable ($C_3$-$C_{12}$)-heterocycloalkyl groups are especially tetrahydrothiophenyl, tetrahydrofuryl, tetrahydropyranyl and dioxanyl.

The expression ($C_6$-$C_{20}$)-aryl encompasses mono- or polycyclic aromatic hydrocarbyl radicals having 6 to 20 carbon atoms. These are preferably ($C_6$-$C_{14}$)-aryl, more preferably ($C_6$-$C_{10}$)-aryl.

Suitable ($C_6$-$C_{20}$)-aryl groups are especially phenyl, naphthyl, indenyl, fluorenyl, anthracenyl, phenanthrenyl, naphthacenyl, chrysenyl, pyrenyl, coronenyl. Preferred ($C_6$-$C_{20}$)-aryl groups are phenyl, naphthyl and anthracenyl.

The expression ($C_3$-$C_{20}$)-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The ($C_3$-$C_{20}$)-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

Suitable ($C_3$-$C_{20}$)-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the $R^1$, $R^2$ and $R^3$ radicals may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —$SO_3H$, —$NH_2$, halogen.

In one embodiment, the $R^1$, $R^2$ and $R^3$ radicals may each independently be substituted by one or more substituents selected from —($C_1$-$C_{12}$)-alkyl, —($C_3$-$C_{12}$)-cycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl.

In one embodiment, the $R^1$, $R^2$ and $R^3$ radicals may each independently be substituted by one or more substituents selected from —($C_1$-$C_{12}$)-alkyl, —($C_3$-$C_{12}$)-cycloalkyl, —O—($C_1$-$C_{12}$)-alkyl, —O—($C_3$-$C_{12}$)-cycloalkyl, —($C_6$-$C_{20}$)-aryl.

In one embodiment, the $R^1$, $R^2$ and $R^3$ radicals may each independently be substituted by one or more substituents selected from —($C_1$-$C_{12}$)-alkyl.

In one embodiment, the $R^1$, $R^2$ and $R^3$ radicals are unsubstituted.

In a preferred embodiment, $R^1$ is —($C_1$-$C_{12}$)-alkyl, preferably —($C_1$-$C_6$)-alkyl, more preferably —($C_1$-$C_4$)-alkyl.

In a preferred embodiment, $R^2$ is —($C_6$-$C_{20}$)-aryl or —($C_3$-$C_{20}$)-heteroaryl.

In one embodiment, if $R^2$ is a heteroaryl radical, $R^2$ is selected from heteroaryl radicals having five to ten ring atoms, preferably five or six ring atoms.

In one embodiment, if $R^2$ is a heteroaryl radical, $R^2$ is selected from heteroaryl radicals having six to ten ring atoms, preferably six ring atoms.

In one embodiment, if $R^2$ is a heteroaryl radical, $R^2$ is selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, $R^2$, if $R^2$ is a heteroaryl radical, is selected from furyl, thienyl, pyrrolyl, imidazolyl, pyridyl, pyrimidyl, indolyl; especially pyrimidyl and imidazolyl; where the heteroaryl radicals mentioned may be substituted as described above.

In one embodiment, $R^2$, if $R^2$ is a heteroaryl radical, is selected from 2-furyl, 2-thienyl, 2-pyrrolyl, 2-imidazolyl, 2-pyridyl, 2-pyrimidyl, 2-indolyl; especially 2-pyrimidyl and 2-imidazolyl; where the heteroaryl radicals mentioned may be substituted as described above.

In one embodiment, $R^2$ is selected from phenyl, pyrimidyl and imidazolyl, preferably phenyl, 2-pyrimidyl and 2-imidazolyl, where the radicals mentioned may be substituted as described above. Preferably, $R^2$ is selected from phenyl, 2-pyrimidyl and N-methylimidazol-2-yl, where the radicals mentioned have no further substitution.

In one embodiment, $R^3$ is selected from heteroaryl radicals having five to ten ring atoms, preferably five or six ring atoms.

In one embodiment, $R^3$ is selected from heteroaryl radicals having six to ten ring atoms, preferably six ring atoms.

In one embodiment, $R^3$ is selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, $R^3$ is selected from furyl, thienyl, pyrrolyl, imidazolyl, pyridyl, pyrimidyl, indolyl, where the heteroaryl radicals mentioned may be substituted as described above.

In one embodiment, $R^3$ is selected from 2-furyl, 2-thienyl, 2-pyrrolyl, 2-imidazolyl, 2-pyridyl, 2-pyrimidyl, 2-indolyl, where the heteroaryl radicals mentioned may be substituted as described above.

In a particularly preferred embodiment, $R^3$ is pyrimidyl or imidazolyl, preferably 2-pyrimidyl and 2-imidazolyl, where the radicals mentioned may be substituted as described above. More particularly, $R^3$ is 2-pyrimidyl or N-methylimidazol-2-yl, where the radicals mentioned have no further substitution.

In one embodiment, $R^1$ is selected from —($C_1$-$C_{12}$)-alkyl; $R^2$ is selected from phenyl, 2-pyrimidyl and 2-imidazolyl; and $R^3$ is selected from 2-pyrimidyl and 2-imidazolyl; where the $R^1$, $R^2$ and $R^3$ radicals may each be substituted as described above.

In one embodiment, the compound has a structure according to one of the formulae (1) and (2):

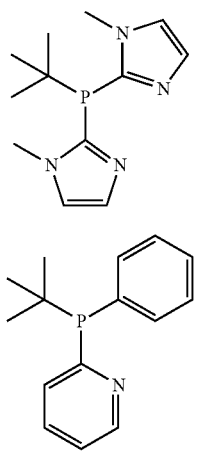

(1)

(2)

The invention further relates to complexes comprising Pd and a monophosphine compound according to the invention. In these complexes, the monophosphine compound according to the invention serves as a ligand for the metal atom. The complexes serve, for example, as catalysts for alkoxycarbonylation. With the complexes according to the invention, it is possible to achieve high yields in the alkoxycarbonylation of a multitude of different ethylenically unsaturated compounds.

The complexes according to the invention may also comprise further ligands which coordinate to the metal atom. These are, for example, ethylenically unsaturated compounds or anions. Suitable additional ligands are, for example, styrene, acetate anions, maleimides (e.g. N-methylmaleimide), 1,4-naphthoquinone, trifluoroacetate anions or chloride anions.

The invention further relates to the use of a monophosphine compound according to the invention for catalysis of an alkoxycarbonylation reaction. The compound according to the invention can especially be used as a metal complex according to the invention.

The invention also relates to a process comprising the process steps of:
a) initially charging an ethylenically unsaturated compound;
b) adding a monophosphine compound according to the invention and a compound comprising Pd,
   or adding a complex according to the invention comprising Pd and a monophosphine compound according to the invention;
c) adding an alcohol;
d) feeding in CO;
e) heating the reaction mixture, with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound comprises 2 to 30 carbon atoms, preferably 6 to 22 carbon atoms, more preferably 8 to 12 carbon atoms, most preferably 8 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents.

In one embodiment, the ethylenically unsaturated compound does not comprise any further functional groups apart from carbon-carbon double bonds.

In a particularly preferred embodiment, the ethylenically unsaturated compound is an unfunctionalized alkene having at least one double bond and 2 to 30 carbon atoms, preferably 6 to 22 carbon atoms, further preferably 8 to 12 carbon atoms, and most preferably 8 carbon atoms.

Suitable ethylenically unsaturated compounds are, for example:
  ethene;
  propene;
  C4 olefins such as 1-butene, cis-2-butene, trans-2-butene, mixture of cis- and trans-2-butene, isobutene, 1,3-butadiene; raffinate I to III, crack-C4
  C5 olefins such as 1-pentene, 2-pentene, 2-methyl-1-butene, 2-methyl-2-butene, 2-methyl-1,3-butadiene (isoprene), 1,3-pentadiene;
  C6 olefins such as tetramethylethylene, 1,3-hexadiene, 1,3-cyclohexadiene;
  C7 olefins such as 1-methylcyclohexene, 2,4-heptadiene, norbornadiene;
  C8 olefins such as 1-octene, 2-octene, cyclooctene, di-n-butene, diisobutene, 1,5-cyclooctadiene, 1,7-octadiene;
  C9 olefins such as tripropene;
  C10 olefins such as dicyclopentadiene;
  undecenes;
  dodecenes;
  internal C14 olefins;
  internal C15 to C18 olefins;
  linear or branched, cyclic, acyclic or partly cyclic, internal C15 to C30 olefins;
  triisobutene, tri-n-butene;
  terpenes such as limonene, geraniol, farnesol, pinene, myrcene, carvone, 3-carene;
  polyunsaturated compounds having 18 carbon atoms, such as linoleic acid or linolenic acid;
  esters of unsaturated carboxylic acids, such as vinyl esters of acetic or propionic acid, alkyl esters of unsaturated carboxylic acids, methyl or ethyl esters of acrylic acid and methacrylic acid, oleic esters, such as methyl or ethyl oleate, esters of linoleic or linolenic acid;
  vinyl compounds such as vinyl acetate, vinylcyclohexene, styrene, alpha-methylstyrene, 2-isopropenylnaphthalene;
  2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2- pentene, 2-methyl-1-butene, 2-methyl-2-butene, 3-methyl-1-butene, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof.

In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the $C_4$ fraction which arises in naphtha cracking and consists essentially of the isomeric n-butenes, isobutane and n-butane after removal of isobutene from raffinate I. Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which are removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the invention is catalysed by the Pd complex according to the invention. The Pd complex may either be added in process step b) as a preformed complex comprising Pd and the phosphine ligands according to the invention or be formed in situ from a compound comprising Pd and the free phosphine ligand. In this context, the compound comprising Pd is also referred to as catalyst precursor.

In the case that the catalyst is formed in situ, the ligand can be added in excess, such that the unbound ligand is also present in the reaction mixture.

In the case of the complex which is added right at the start as well, it is additionally possible to add further ligand, such that unbound ligand is also present in the reaction mixture.

In one variant, the compound comprising Pd is selected from palladium chloride ($PdCl_2$), palladium(II) acetylacetonate [$Pd(acac)_2$], palladium(II) acetate [$Pd(OAc)_2$], dichloro(1,5-cyclooctadiene)palladium(II) [$Pd(cod)_2Cl_2$], bis(dibenzylideneacetone)palladium [$Pd(dba)_2$], bis(acetonitrile)dichloropalladium(II) [$Pd(CH_3CN)_2Cl_2$], palladium (cinnamyl) dichloride [$Pd(cinnamyl)Cl_2$].

Preferably, the compound comprising Pd is $PdCl_2$, $Pd(acac)_2$ or $Pd(OAc)_2$. $PdCl_2$ is particularly suitable.

The alcohol in process step c) may be branched or linear, cyclic, alicyclic, partly cyclic or aliphatic, and is especially a $C_1$- to $C_{30}$-alkanol. It is possible to use monoalcohols or polyalcohols.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, aryl, heteroaryl or silyl groups and/or halogen substituents.

In one embodiment, the alcohol does not comprise any further functional groups except for hydroxyl groups.

The alcohol may contain unsaturated and aromatic groups. However, it is preferably an aliphatic alcohol.

An aliphatic alcohol in the context of this invention refers to an alcohol which does not comprise any aromatic groups, i.e., for example, an alkanol, alkenol or alkynol.

In one embodiment, the alcohol is an alkanol having one or more hydroxyl groups and 1 to 30 carbon atoms, preferably 1 to 22 carbon atoms, more preferably 1 to 12 carbon atoms, most preferably 1 to 6 carbon atoms.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, phenol, 2-ethylhexanol, isononanol, 2-propylheptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

In one variant of the process, the alcohol in process step c) is selected from the group of the polyalcohols.

In one variant of the process, the alcohol in process step c) is selected from: diols, triols, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethyl-propane-1,3-diol, 1,2,6-trihydroxyhexane, pentaerythritol, 1,1,1-tri(hydroxymethyl)ethane, catechol, resorcinol and hydroxyhydroquinone.

In one variant of the process, the alcohol in process step c) is selected from: sucrose, fructose, mannose, sorbose, galactose and glucose.

In a preferred embodiment of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the ethylenically unsaturated compound to an ester.

The molar ratio of the ethylenically unsaturated compound initially charged in step a) to the alcohol added in step c) is preferably between 1:1 and 1:20, more preferably 1:2 to 1:10, more preferably 1:3 to 1:4.

The mass ratio of Pd to the ethylenically unsaturated compound initially charged in step a) is preferably between 0.001% and 0.5% by weight, preferably between 0.01% and 0.1% by weight, more preferably between 0.01% and 0.05% by weight.

The molar ratio of the monophosphine compound according to the invention to Pd is preferably between 0.1:1 and 400:1, preferably between 0.5:1 and 400:1, more preferably between 1:1 and 100:1, most preferably between 2:1 and 50:1.

Preferably, the process is conducted with addition of an acid. In one variant, the process therefore additionally comprises step c'): adding an acid to the reaction mixture. This may preferably be a Brønsted or Lewis acid.

Suitable Brønsted acids preferably have an acid strength of $pK_a \leq 5$, preferably an acid strength of $pK_a \leq 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, more preferably 0.5 to 5 mol %, most preferably 0.6 to 3 mol %, based on the molar amount of the ethylenically unsaturated compound used in step a).

EXAMPLES

The invention is described in detail hereinafter by working examples.

General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}P$ NMR signals were referenced as follows: $SR_{31P} = SR_{1H} * (BF_{31P}/BF_{1H}) = SR_{1H} * 0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of chloro-2-pyridyl-tert-butylphosphine (Precursor A)

The Grignard for the synthesis of chloro-2-pyridyl-t-butylphosphine is prepared by the "Knochel method" with isopropylmagnesium chloride (Angew. Chem. 2004, 43, 2222-2226). The workup is effected according to the method of Budzelaar (Organometallics 1990, 9, 1222-1227).

Scheme 1: Synthesis of precursor A

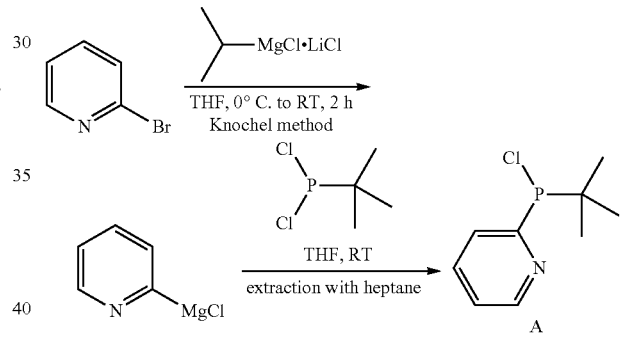

8.07 ml of a 1.3 M isopropylmagnesium chloride solution (Knochel's reagent) are introduced into a 50 ml round-bottom flask with magnetic stirrer and septum, and cooled to −15° C. Thereafter, 953.5 μl (10 mmol) of 2-bromopyridine are rapidly added dropwise. The solution immediately turns yellow. It is allowed to warm up to −10° C. The conversion of the reaction is determined as follows: about 100 μl solution are taken and introduced into 1 ml of a saturated ammonium chloride solution. If the solution "bubbles", not much Grignard has formed yet. The aqueous solution is extracted with a pipette of ether and the organic phase is dried over $Na_2SO_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion. Now the Grignard solution can be slowly added dropwise with a syringe pump to a solution of 1.748 g (11 mmol) of dichloro-tert-butylphosphine in 10 ml of THF which has been cooled to −15° C. beforehand. It is important that the dichloro-tert-butylphosphine solution is cooled. At room temperature, considerable amounts of dipyridyl-tert-butylphosphine would be obtained. A clear yellow solution is initially formed, which then turns cloudy. The mixture is left to warm up to room temperature and to stir overnight. According to GC-MS, a large amount of product has formed. The solvent is removed under high vacuum and a whitish solid which is brown in places is obtained. The solid is suspended with 20 ml of heptane and the solid is comminuted in an ultrasound bath. After allowing the white solid to settle out, the solution is decanted. The operation is repeated twice with 10-20 ml each time of heptane. After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data: $^1$H NMR (300 MHz, $C_6D_6$): δ 8.36 (m, 1H, Py), 7.67 (m, 1H, Py), 7.03-6.93 (m, 1H, Py), 6.55-6.46 (m, 1H, Py), 1.07 (d, J=13.3 Hz, 9H, t-Bu).

$^{13}$C NMR (75 MHz, $C_6D_6$): δ 162.9, 162.6, 148.8, 135.5, 125.8, 125.7, 122.8, 35.3, 34.8, 25.9 and 25.8.

$^{31}$P NMR (1213 MHz, $C_6D_6$) δ 97.9.

MS (EI) m:z (relative intensity) 201 (M$^+$, 2), 147 (32), 145 (100), 109 (17), 78 (8), 57.1 (17).

Preparation of Compound 1

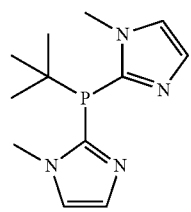

(1)

0.78 g (9.5 mmol) of 1-methylimidazole are weighed out in a 50 ml three-neck flask with thermometer and dropping funnel under argon and dissolved in 10 ml of THF. Then 1.6 ml of TMEDA are added to the solution. The mixture is then cooled down to −78° C. Thereafter, 6 ml of 1.6 N n-butyllithium in hexane are added dropwise by means of a dropping funnel. The 50 ml flask containing the reaction mixture is left to stir at room temperature for 30 min. Subsequently, 1.5 g of tert-butyldichlorophosphine are dissolved in 20 ml of THF. Then the 1-methylimidazole-BuLi mixture is added dropwise to the tert-butyldichlorophosphine at −78° C. Thereafter, the mixture is warmed to room temperature. A product precipitates out. The suspension is filtered and the residue is dissolved in water and then washed three times with dichloromethane. The organic phase is dried with $Na_2SO_4$ and then the solvent is removed under reduced pressure. The residue is dissolved with 5 ml of dichloromethane and blanketed with 20 ml of diethyl ether. The product crystallizes. The product was obtained in an amount of 0.8 g.

Purity (NMR)=98%, $^{31}$P NMR ($CD_2Cl_2$, 121 MHz)=−32.25 ppm, $^{13}$C NMR ($CD_2Cl_2$, 75 MHz)=144 s, 130.2 d ($J_{PC}$=3.7 Hz), 123.8 s, 34.2 d, ($J_{PC}$=11.7 Hz), 25.9 d, ($J_{PC}$=14.3 Hz)

$^1$H NMR ($CD_2Cl_2$, 300 MHz): 7.04, d, (J=1 Hz, 1H), 6.94 dd (J=1 Hz, J=1.5 Hz, 1H), 3.4 s (6H), 1.2 d (J=14.6 Hz, 9H)

HRMS: calculated for $C_{12}H_{19}N_4P$: 251.14201, found: 251.14206.

Preparation of 2-(tert-butyl(phenyl)phosphino)pyridine (Compound 2)

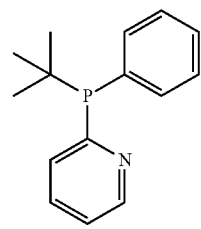

(2)

3.4 g (16.8 mmol) of 2-(tert-butylchlorophosphino)pyridine (precursor A) are dissolved under argon in 50 ml of absolute diethyl ether in a 100 ml three-neck flask provided with a low-temperature thermometer and magnetic stirrer. The mixture is cooled down to −78° C. At this temperature, within 10 minutes, 10 ml of a 1.8 N phenyllithium solution (in dibutyl ether) are added by means of a dropping funnel. The mixture is stirred at this temperature for 10 minutes and then warmed to room temperature and stirred for a further half an hour. This solution is washed three times with 10 ml of degassed water. The organic phase is then distilled under a fine vacuum of 10$^{-1}$ Torr. The product is obtained at this pressure at 130° C. as a clear liquid in a high purity of greater than 97% (NMR). The yield is 3.85 g (93%).

Analysis:

$^{31}$P (acetone-$d_6$, 121 MHz), 16.31 s, $^{13}$C (75 MHz, acetone-$d_6$, 165.1 (d, $J_{PC}$=10.5 Hz), 150.3 (d, $J_{PC}$=5 Hz), 137.3 s, 137.0 s, 136.7 s, 135.9 d, 135.9 (d, $J_{PC}$=7.6 Hz), 131.1 s, 130.6 s, 130.2 s, 128.9 (d, $J_{PC}$=8 Hz), 122.9 s, 32.1 (d, $J_{PC}$=13.1 Hz), 28.5 (d, $J_{PC}$=13.7 Hz), $^1$H (acetone-$d_6$, 300 MHz):

8.74 (dm, J=4.7 Hz), 7.7-7.6 m (2H), 7.4-7.3 (m, 3H), 7.28-7.23 (m, 1H), 1.2 (d, J=12.6 Hz, 9H)

MS (EI, 70 eV): m/z (%), 243 (M+, 17), 203 (65), 187 (78), 156 (6), 126 (8), 109 (100), 78 (11), 57 (11), HRMS (EI), calculated for C15H18N1P1: 243.11714, found: 243.11753.

Further Ligands

The following comparative compounds are commercially available.

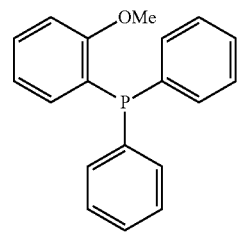

3 (CE)

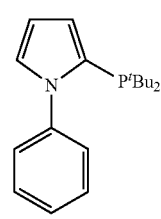

10 (CE)

CE: Comparative example

Alkoxycarbonylation Experiments

General Experiment Description for Reactions in Batch-wise Mode:

The appropriate amounts of substrate, palladium salt, acid and alcohol are mixed under argon in a 50 ml Schlenk vessel while stirring with a magnetic stirrer.

A 100 ml steel autoclave from Parr provided with a gas inlet and a gas outlet valve, a digital pressure transducer, a temperature sensor and a ball valve, and an installed capillary for sampling, is freed of oxygen by means of vacuum and argon purging three times. Subsequently, the reaction solution from the Schlenk vessel is introduced by means of a capillary into the autoclave in an argon counterflow through the ball valve. Subsequently, either the appropriate amount of CO is injected at room temperature and then the autoclave is heated up to reaction temperature (reactions that are not run under constant pressure) or the autoclave is first heated up to reaction temperature and then the CO is injected by means of a burette connected to the autoclave by means of a pressure reducer. This burette is then filled with CO to about 100 bar and, during the reaction, supplies the CO required at a constant pressure. This burette has a dead volume of about 30 ml and is provided with a digital pressure transducer. Then the reaction is conducted at the required temperature for the required time while stirring. In the course of this, by means of software (Specview from SpecView Corporation) and a Parr 4870 process controller and a 4875 power controller, data for the pressure variation in the autoclave and in the gas burette are recorded. These data are used to generate Excel tables, which are used at a later stage to create diagrams which show gas consumptions and hence conversions over time. If required, via the capillary, the GC samples are collected and analysed. For this purpose, a suitable exact amount (2-10 ml) of isooctane as internal standard is also added to the Schlenk vessel before the reaction. These also give information about the course of the reaction. At the end of the reaction, the autoclave is cooled down to room temperature, the pressure is cautiously released, isooctane is added if necessary as internal standard, and a GC analysis or, in the case of new products, a GC-MS analysis is conducted.

General Experimental Method for Autoclave Experiments in Glass Vials

A 300 ml Parr reactor is used. Matched to this is an aluminium block of corresponding dimensions which has been manufactured in-house and which is suitable for heating by means of a conventional magnetic stirrer, for example from Heidolph. For the inside of the autoclave, a round metal plate of thickness about 1.5 cm was manufactured, containing 6 holes corresponding to the external diameter of the glass vials. Matching these glass vials, they are equipped with small magnetic stirrers. These glass vials are provided with screw caps and suitable septa and charged, using a special apparatus manufactured by glass blowers, under argon with the appropriate reactants, solvents and catalysts and additives. For this purpose, 6 vessels are filled at the same time; this enables the performance of 6 reactions at the same temperature and the same pressure in one experiment. Then these glass vessels are closed with screw caps and septa, and a small syringe cannula of suitable size is used to puncture each of the septa. This enables gas exchange later in the reaction. These vials are then placed in the metal plate and these are transferred into the autoclave under argon. The autoclave is purged with CO and filled at room temperature with the CO pressure intended. Then, by means of the magnetic stirrer, under magnetic stirring, the autoclave is heated to reaction temperature and the reaction is conducted for the appropriate period. Subsequently, the autoclave is cooled down to room temperature and the pressure is slowly released. Subsequently, the autoclave is purged with nitrogen. The vials are taken from the autoclave, and a defined amount of a suitable standard is added. A GC analysis is effected, the results of which are used to determine yields and selectivities.

Analysis:

Methanol Analysis

Methanol was pretreated in a solvent drying system: Pure Solv MD Solvent Purification System, from Innovative Technology Inc., One Industrial Way, Amesbury Mass. 01013

Water Values:

Determined by Karl Fischer Titration: TitraLab 580-TIM580, from Radiometer Analytical SAS (Karl Fischer titration), water content: measurement ranges: 0.1-100% w/w, water content measured: 0.13889%

The following were used:

Technical-grade methanol: Applichem: Nr A2954,5000, batch number: LOT: 3L005446, water content max. 1%

Methanol: Acros Organics (over molecular sieve): water content 0.005%, code number: 364390010, batch number: LOT 1370321

Methoxycarbonylation of Ethene

A 50 ml Schlenk vessel was charged with Pd(acac)$_2$ (6.53 mg, 0.04 mol %), ligand (0.16 mol %), ethene (1.5 g, 53 mmol), 20 ml of methanol and para-toluenesulphonic acid (PTSA, 61 mg, 0.6 mol %). The reaction mixture was transferred by means of a capillary in an argon counterflow into a 100 ml steel autoclave as described above. The CO pressure was adjusted to 40 bar. The reaction proceeded at 80° C. for 3 hours. On conclusion of the reaction, the autoclave was cooled down to room temperature and cautiously decompressed.

Isooctane (100 μl) was added as internal GC standard. Yield and selectivity were determined by means of GC.

The results are shown in the following table:

| Ligand | Yield |
|---|---|
| 1 | 30% |
| 2 | 14% |
| 3 (CE) | 3% |
| 10 (CE) | 0% |

CE: comparative example

This example shows that the inventive ligands 1, 2 achieve much better yields in the methoxycarbonylation of ethene than the comparative ligands 3 and 10.

Isomerizing Regioselective Methoxycarbonylation of 1-Octene

Scheme 8: Regioselective methoxycarbonylation of 1-octene; the reaction leads, aside from terminal methoxycarbonylation, mainly to a side reaction in the 2 position (referred to as major).

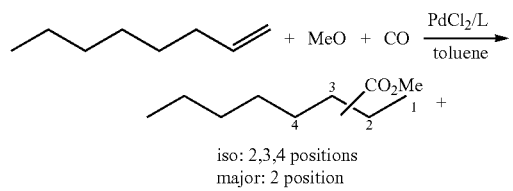

iso: 2,3,4 positions
major: 2 position

-continued

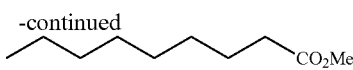

The iso/n ratio reported hereinafter indicates the ratio of olefins converted internally to esters to olefins converted terminally to esters.

a) Variant with PdCl$_2$

A 4 ml vial was charged with PdCl$_2$ (1.77 mg, 1.0 mol %) and ligand (4.0 mol %), and a magnetic stirrer bar was added. Then toluene (2 ml), 1-octene (157 µl, 1 mmol) and MeOH (40.5 µl, 1 mmol) were injected with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane (100 µl) was added as internal GC standard. Yield and regioselectivity were determined by means of GC.

The results are shown in the following table:

| Ligand | Yield | iso/n |
| --- | --- | --- |
| 2 | 75% | 28/72 |
| 3 (CE) | 87% | 55/45 |
| 10 (CE) | 10% | 45/55 |

CE: comparative example;
Cy: cyclohexyl;
o-tol: ortho-tolyl;
Ph: phenyl;
$^t$Bu: tert-butyl.

The inventive ligand 2 features both a higher yield and a high n/iso selectivity. By contrast, the ligand 10 known from the prior art achieves only a low yield and is additionally not regioselective. The comparative ligand 3 does achieve a high yield, but is likewise not regioselective.

b) Variant with Pd(acac)$_2$

A 25 ml Schlenk vessel was charged with [Pd(acac)$_2$] (1.95 mg, 0.04 mol %), p-toluenesulphonic acid (PTSA) (18.24 µl, 0.6 mol %) and MeOH (10 ml). A 4 ml vial was charged with the ligand (0.16 mol %), and a magnetic stirrer bar was added. Thereafter, 1.25 ml of the clear yellow solution from the Schlenk vessel and 1-octene (315 µl, 2 mmol) were injected with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane (100 µl) was added as internal GC standard. Yield and regioselectivity were determined by means of GC.

The results are shown in the following table:

| Ligand | Yield | iso/n |
| --- | --- | --- |
| 2 | 26% | 74/26 |
| 3 (CE) | 16% | 77/23 |
| 10 (CE) | 0% | N/A |

CE: comparative example

Here too, the inventive ligand 2 exhibits a high iso/n selectivity and a higher yield than comparative ligands 3 and 10.

The invention claimed is:

1. Compound of formula (I)

where
R$^1$ is selected from the group consisting of —(C$_1$-C$_{12}$)-alkyl, —(C$_3$-C$_{12}$)-cycloalkyl and —(C$_3$-C$_{12}$)-heterocycloalkyl;
R$^2$ is selected from the group consisting of phenyl, pyrimidyl and 2-imidazolyl;
R$^3$ is 2-imidazolyl;
and R$^1$, R$^2$ and R$^3$ may each independently be substituted by one or more substituents selected from the group consisting of —(C$_1$-C$_{12}$)-alkyl, —(C$_3$-C$_{12}$)-cycloalkyl, —(C$_3$-C$_{12}$)-heterocycloalkyl, —O—(C$_1$-C$_{12}$)-alkyl, —O—(C$_1$-C$_{12}$)-alkyl-(C$_6$-C$_{20}$)-aryl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —CO—(C$_1$-C$_{12}$)-alkyl, —CO—(C$_3$-C$_{12}$)-cycloalkyl, —N—[(C$_1$-C$_{12}$)-alkyl]$_2$, —(C$_6$-C$_{20}$)-aryl, —(C$_6$-C$_{20}$)-aryl-O—(C$_1$-C$_{12}$)-alkyl, —(C$_3$-C$_{20}$)-heteroaryl, —(C$_3$-C$_{20}$)-heteroaryl-(C$_1$-C$_{12}$)-alkyl, —(C$_3$-C$_{20}$)-heteroaryl-O—(C$_1$-C$_{12}$)-alkyl, —COOH, —OH, —SO$_3$H, —NH$_2$ and halogen.

2. Compound according to claim 1, where R$^1$ is —(C$_1$-C$_{12}$)-alkyl.

3. A compound having formulae (1)

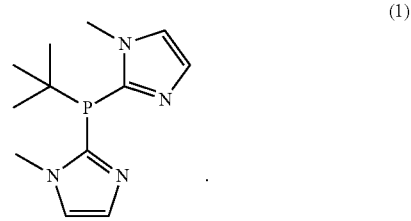 [SMILES: Cn1ccnc1P(c1nccn1C)C(C)(C)C]

4. Complex comprising Pd and a compound of formula (I)

where
R$^1$ is selected from the group consisting of —(C$_1$-C$_{12}$)-alkyl, —(C$_3$-C$_{12}$)-cycloalkyl and —(C$_3$-C$_{12}$)-heterocycloalkyl;
R$^2$ is selected from the group consisting of phenyl, pyrimidyl and 2-imidazolyl;
R$^3$ is imidazolyl;
and R$^1$, R$^2$ and R$^3$ may each independently be substituted by one or more substituents selected from the group consisting of —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$ and halogen.

5. Process comprising the following process steps:
a) initially charging an ethylenically unsaturated compound;
b) adding a compound of formula (I)

(I)

where
$R^1$ is selected from the group consisting of —($C_1$-$C_{12}$)-alkyl, —($C_3$-$C_{12}$)-cycloalkyl and —($C_3$-$C_{12}$)-heterocycloalkyl;
$R^2$ is selected from the group consisting of phenyl, pyrimidyl and 2-imidazolyl;
$R^3$ is imidazolyl;
and $R^1$, $R^2$ and $R^3$ may each independently be substituted by one or more substituents selected from the group consisting of —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$ and halogen, and a compound comprising Pd,
or adding a complex according to claim 4;
c) adding an alcohol;
d) feeding in CO;
e) heating the reaction mixture, with conversion of the ethylenically unsaturated compound to an ester.

6. Process according to claim 5,
wherein the ethylenically unsaturated compound is selected from the group consisting of ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, and mixtures thereof.

7. Process according to claim 5,
wherein the compound comprising Pd in process step b) is selected from the group consisting of palladium dichloride, palladium(II) acetylacetonate, palladium(II) acetate, dichloro(1,5-cycloocta-diene)palladium(II), bis(dibenzylideneacetone)palladium, bis(acetonitrile)dichloro-palladium(II) and palladium(cinnamyl) dichloride.

8. Process according to claim 5,
wherein the alcohol in process step c) is selected from the group consisting of methanol, ethanol, 1-propanol, 1-butanol, 1-pentanol, 1-hexanol, 2-propanol, tert-butanol, 3-pentanol, cyclohexanol, phenol and mixtures thereof.

9. Process according to claim 5, wherein the alcohol in process step c) is an aliphatic alcohol.

10. A process for catalysis of an alkoxycarbonylation reaction, comprising: introducing a compound of formula (I)

(I)

where
$R^1$ is selected from the group consisting of —($C_1$-$C_{12}$)-alkyl, —($C_3$-$C_{12}$)-cycloalkyl and —($C_3$-$C_{12}$)-heterocycloalkyl;
$R^2$ is selected from the group consisting of phenyl, pyrimidyl and 2-imidazolyl;
$R^3$ is imidazolyl;
and $R^1$, $R^2$ and $R^3$ may each independently be substituted by one or more substituents selected from the group consisting of
—($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$ and halogen or a complex according to claim 4.

* * * * *